(12) United States Patent
Delamarche et al.

(10) Patent No.: US 9,421,540 B2
(45) Date of Patent: Aug. 23, 2016

(54) MICROFLUIDIC DEVICE WITH AUXILIARY AND BYPASS CHANNELS

(75) Inventors: Emmanuel Delamarche, Rueschlikon (CH); Luc Gervais, Rueschlikon (CH); Martina Hitzbleck, Rueschlikon (CH)

(73) Assignee: International Business Machines Corporation, Armonk, NY (US)

(*) Notice: Subject to any disclaimer, the term of this patent is extended or adjusted under 35 U.S.C. 154(b) by 95 days.

(21) Appl. No.: 13/881,975

(22) PCT Filed: Aug. 3, 2011

(86) PCT No.: PCT/IB2011/053456
§ 371 (c)(1),
(2), (4) Date: Sep. 3, 2013

(87) PCT Pub. No.: WO2012/056334
PCT Pub. Date: May 3, 2012

(65) Prior Publication Data
US 2013/0337578 A1    Dec. 19, 2013

(30) Foreign Application Priority Data

Oct. 28, 2010 (EP) .................................... 10189178

(51) Int. Cl.
*B01L 3/00* (2006.01)
*B01F 5/04* (2006.01)
(Continued)

(52) U.S. Cl.
CPC ............. *B01L 3/5027* (2013.01); *B01F 5/0498* (2013.01); *B01F 13/0059* (2013.01);
(Continued)

(58) Field of Classification Search
CPC .......... B01L 2300/0864; B01L 3/5027; G01N 15/1484

USPC .......................................... 422/502; 436/180
See application file for complete search history.

(56) References Cited

U.S. PATENT DOCUMENTS 6,591,852 B1 * 7/2003 McNeely et al. ............... 137/14
6,656,744 B2 12/2003 Pronovost et al.
(Continued)

FOREIGN PATENT DOCUMENTS

EP    1 525 916 A1    4/2005
FR    2 545 685 A1    11/1984
(Continued)

OTHER PUBLICATIONS

Kartalov, "Multiplexed microfluidic immunoassays for point-of-care in vitro diagnostics," Assay Development, Feature Articles, Sep. 2006, http://www.ivdtecnology.com/article/multiplexed-microfluidic-immunoassays-for-point-of-care-in-viro-diagnostics, last printed Oct. 18, 2010, pp. 1-4.
(Continued)

*Primary Examiner* — Christopher A Hixson
*Assistant Examiner* — Emily Berkeley
(74) *Attorney, Agent, or Firm* — Scully, Scott, Murphy & Presser, P.C.; Jennifer Davis, Esq.

(57) ABSTRACT

A microfluidic device is provided. The microfluidic device has: a flow inlet and a flow outlet; a bypass channel defining a first flow path away from the flow inlet and toward the flow outlet; and an auxiliary channel defining a second flow path away from the flow inlet and toward the flow outlet, wherein the auxiliary channel defines a reagent area adapted to receive a reagent, and wherein the auxiliary channel joins the bypass channel at a primary junction downstream from the reagent area and upstream from the flow outlet.

11 Claims, 4 Drawing Sheets

(51) Int. Cl.
*B01F 13/00* (2006.01)
*G01N 15/14* (2006.01)

(52) U.S. Cl.
CPC ...... *B01L 3/502746* (2013.01); *B01L 2200/16* (2013.01); *B01L 2300/0816* (2013.01); *B01L 2300/0864* (2013.01); *B01L 2300/0867* (2013.01); *B01L 2400/086* (2013.01); *G01N 15/1484* (2013.01); *Y10T 436/2575* (2015.01)

(56) References Cited

U.S. PATENT DOCUMENTS

| | | | |
|---|---|---|---|
| 7,749,775 | B2 | 7/2010 | Maher et al. |
| 2004/0109790 | A1 | 6/2004 | Shartle et al. |
| 2004/0206408 | A1* | 10/2004 | Peters et al. ............ 137/825 |
| 2005/0113101 | A1 | 5/2005 | Hansen et al. |
| 2005/0118070 | A1* | 6/2005 | Griss ............ B01L 3/502738 422/400 |
| 2005/0133101 | A1 | 6/2005 | Chung et al. |
| 2006/0018790 | A1* | 1/2006 | Naka et al. ............ 422/58 |
| 2008/0014575 | A1 | 1/2008 | Nelson |
| 2009/0317793 | A1 | 12/2009 | Jonsmann et al. |
| 2010/0173397 | A1 | 7/2010 | Esfandiari |
| 2010/0261286 | A1 | 10/2010 | Kim et al. |

FOREIGN PATENT DOCUMENTS

| | | |
|---|---|---|
| FR | 2 688 709 A1 | 9/1993 |
| JP | H10-132712 A | 5/1998 |
| JP | 2002-243734 A | 8/2002 |
| JP | 2002-527250 A | 8/2002 |
| JP | 2003-507737 A | 2/2003 |
| JP | 2004225912 A | 8/2004 |
| JP | 2005-181295 A | 7/2005 |
| JP | 2008532005 A | 8/2008 |
| WO | 00/22436 A1 | 4/2000 |
| WO | 01/14865 A1 | 3/2001 |
| WO | 2008/119470 A1 | 10/2008 |
| WO | WO 2008130623 A1 * | 10/2008 |

OTHER PUBLICATIONS

Zhou et al., "Immunoassay on Cotton Yarn for Low-Cost Diagnostics," Biomedical Engineering, McGill University, Montreal, Canada, , 14th International Conference on Miniaturized Systems for Chemistry and Life Sciences, Oct. 3-7, 2010, Groningen, The Netherlands, pp. 25-27.
Lou et al., "PDMS microfludic device for optical detection of protein immunoassay using gold nanoparticles," Advance Article on the web Apr. 19, 2005, Accepted Mar. 31, 2005, Lab Chip, 2005, 5, pp. 726-729.
English language abstract FR 2 688 709.
English language abstract FR 2 545 685.
International Search Report PCT/IB2011/053456.
Chinese Office Action dated Jun. 11, 2014 from the corresponding Chinese application 201180051256X.
Examination Report, dated Sep. 19, 2014, from the corresponding Great Britain application.
Stevens et al., "Enabling a microfluidic immunoassay for the developing world by integration of on-card dry reagent storage", The Royal Society of Chemistry, Lab Chip, 2008, first published as Advance Article on the web Oct. 16, 2008, Accepted Aug. 19, 2008, pp. 2038-2045.
Gervais et al., "Toward one-step point-of-care immunodiagnostics using capillary-driven microfluidics and PDMS substrates", The Royal Society of Chemistry, Lab Chip, 2009, first published as Advance Article on the web Aug. 21, 2009, Accepted Jul. 28, 2009, pp. 3330-3337.
Garcia et al., "Controlled microfluidic reconstitution of functional protein from an anhydrous storage depot", The Royal Society of Chemistry, Lab Chip, 2004, first published as Advance Article on the web Dec. 9, 2003, Accepted Nov. 5, 2003, pp. 78-82.
Gervais et al., "One-Step Immunoassay on Capillary Driven Microfluidics", Twelfth International conference on Miniaturized Systems for Chemistry and Life Sciences. Oct. 12-16, 2008, San Diego, California, USA, pp. 1949-1951.
Zimmermann, "Autonomous Capillary Systems for Life Science Research and Medical Diagnostics", Basel, Oct. 2007, URL: http://edoc.unibas.ch/1036/1/Diss.pdf.

\* cited by examiner

MICROFLUIDIC DEVICE WITH AUXILIARY AND BYPASS CHANNELS

FIELD OF THE INVENTION

The invention relates in general to the field of microfluidic devices, and in particular, to ligand-receptor assay or immunoassay devices.

BACKGROUND OF THE INVENTION

Microfluidic devices are generally known, including immunoassay devices. Easy-to-use immunoassay devices are generally desired for point-of-care applications. For instance, "one-step" (immuno)assays akin the well known pregnancy test have been developed, wherein all reagents needed to detect an analyte of interest in a sample are integrated into the device during manufacturing. A non-expert user only needs to add a sample in a sample-receiving structure of the device. From there, the sample flows and redissolves the reagents, which then react with the analyte so as to make it detectable by means of, for example, optical or electrochemical methods. Typically, detection of analytes that have been reacted with the reagents occurs in a region of the device that is located after the area containing the reagents.

Point-of-care diagnostics should benefit from miniaturization based on microfluidics because microfluidics integrate functions that can together preserve valuable samples and reagents, increase sensitivity of a test, and accelerate mass transport limited reactions. Detection of several analytes in parallel is also facilitated by miniaturization. Finally, miniaturization increases the portability of diagnostics by reducing their size and weight. However, a challenge is to incorporate reagents into microfluidics and to make the devices simple to use. Yet another challenge is to make devices for one-step assays disposable and cheap to manufacture. For this reason, devices for one-step assays rarely have actuation mechanisms that interact with flow of liquids and reagents.

L. Gervais and E. Delamarche have recently demonstrated a concept for one-step immunoassays using microfluidic chips (Lab Chip, 2009, 9, 3330-3337). More in detail, the authors have integrated reagents such as detection antibodies (dAbs) and capture antibodies (cAbs) with microfluidic functional elements for detecting analyte molecules inside a sample using a one-step immunoassay: the integrated device only requires the addition of sample to trigger a cascade of events powered by capillary forces for effecting a sandwich immunoassay that is read using a fluorescence microscope. The microfluidic elements comprise a sample collector, delay valves, flow resistors, a deposition zone for dAbs, a reaction chamber sealed with a polydimethylsiloxane (PDMS) substrate, and a capillary pump and vents. Parameters for depositing 3.6 nL of a solution of dAb on the chip using an inkjet are optimized. This deposition by means of an inkjet is sometimes termed "spotting". The PDMS substrate is patterned with receptors for analytes, which provide signal areas as well as positive control areas. Various storage conditions of the patterned PDMS were investigated for up to 6 months, revealing that storage with a desiccant preserved at least 51% of the activity of the cAbs. C-reactive protein (CRP), a general inflammation and cardiac marker, was detected with this one-step chip using only 5 μL of human serum, by measuring fluorescent signals from 30×100 μm$^2$ areas of the PDMS substrate in the wet reaction chamber. In this example, the one-step chip can detect CRP at a concentration of 10 ng mL$^{-1}$ in less than 3 min and below 1 ng mL$^{-1}$ within 14 min.

Figure 1A:
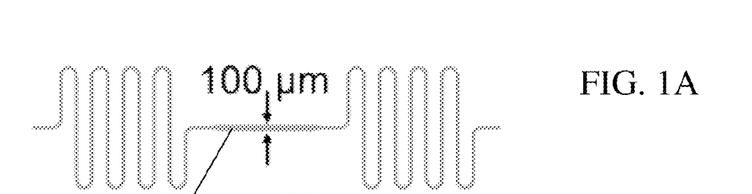
FIGS. 1A-C (prior art) schematically depict channel structures of known microfluidic devices.
Figure 1B:
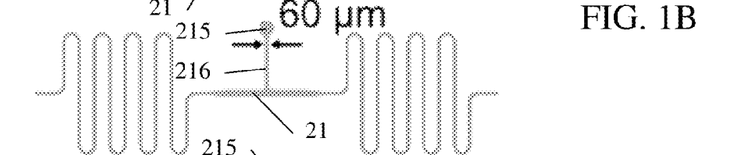
Figure 1C:
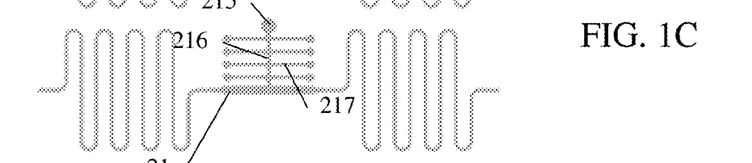

In the above paper, three types of structures for spotting and dissolving the dAbs are disclosed, which are reproduced here on FIG. 1A-C. Namely:

FIG. 1A depicts a structure with main straight channel 21;

FIG. 1B shows a structure with a main channel 21, side connector 216 and spotting target 215; and FIG. 1C shows a structure with a main channel 21, a plurality of side connectors 216, 217 and spotting target 215.

The geometries of said structures were developed with the sake of miniaturization (for better assay performances) while bringing spotted dAbs directly on the sample flow path or near to it so that dAbs can dissolve in the sample flowing through the device. Spotting small volumes of liquids in such devices (i.e., a few nL or tens of nL) is challenging but can be achieved thanks to inkjet technology.

More in detail, in FIG. 1A, it is difficult to position an inkjet over the main straight channel and the volume of dAb solution spotted must be kept small to prevent overflow or spreading of the spotted solution throughout the flow path defined therein. The structure of FIG. 1B and specially that of FIG. 1C helps relaxing the accuracy needed for spotting, thanks to the larger circular target area 215 on top of the side connector 216. Adding branching channels 217 furthermore gives the possibility to accommodate more spotted liquid, which might be needed to increase the amount of dAb available for a given test (e.g. high analyte concentration).

Figure 1D:
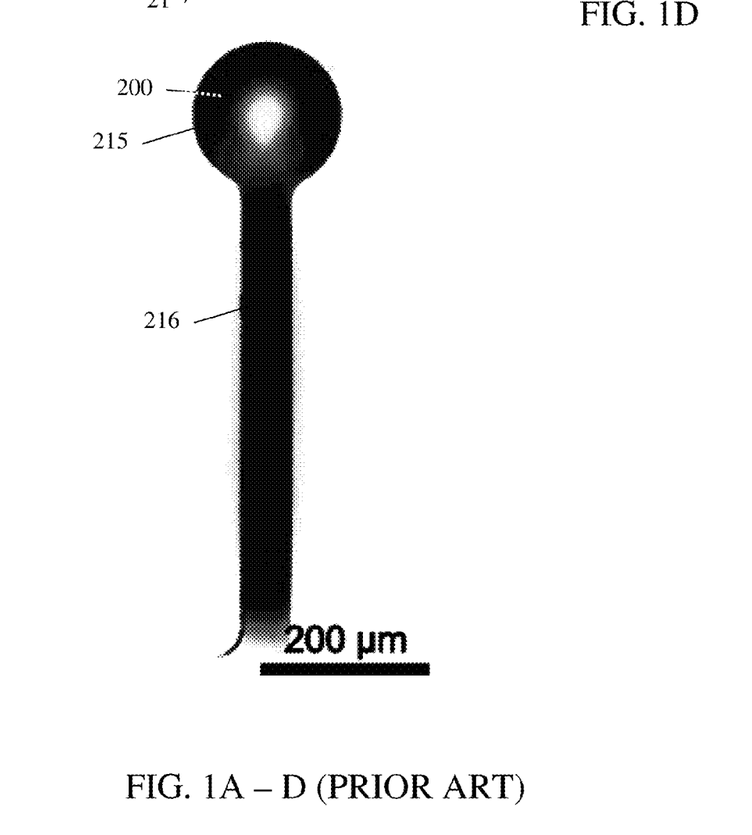
FIG. 1D (prior art) is a negative, grayscaled fluorescence microscope image showing detection antibodies (dAbs) in a deposition zone (circular area) on top of a side connector of a central channel (as in FIG. 1B), after spotting and drying.

Next, FIG. 1D is a negative, grayscaled fluorescence microscope image showing the dAbs 200 in the deposition zone 215 (of FIG. 1B) after spotting and drying. Although the dAbs are clearly located inside the microstructures, an air bubble may form as soon as the sample starts entering the deposition zone. Moreover, most of the spotted dAbs may not diffuse/flow outside the deposition zone in that case.

In fact, the sensitivity of an assay is strongly affected by the time during which dAbs bind to analytes and surface-immobilized receptors and the volume of sample in which dAbs dissolve. There is a time/volume equivalence due to the flow rate equation: t=V/Q, where t is the time needed to displace a given volume V at a flow rate Q.

In a one-step assay, it might be realized that the dissolution profile of dAbs is hard to optimize because, ideally, no actuation on Q, the flow rate, is performed by an operator or instrument. Actuation of Q on a chip is possible but requires expensive and complex devices and a source of power for actuation.

To summarize, a structure with a main straight channel section as in FIG. 1A makes it challenging for spotting, owing to the x, y-in plane accuracy required, and a limited volume can be spotted. Moreover, it typically leads to a (too) fast dissolution of the spotted dAbs (typically 30 seconds), which in turn leads to a small volume only of sample containing the dAbs. In a microfluidic device (or miniaturized system), it might be realized that a liquid can dissolve reagents that are placed on a liquid path too efficiently. If reagents are too quickly dissolved, they may not be present in the correct volume fraction of liquid for a given test. For instance, dAbs that are too quickly dissolved will be present mostly at the filling front of a sample. These dAbs will not be able to react with many analytes in the sample and will quickly move over receptor areas without giving sufficient time for the receptors to gradually bind analytes and dAbs. Therefore, the efficiency of microfluidic devices in moving liquids and dissolving reagents can be (paradoxically) counterproductive.

Some examples of how to slow the release of reagents in microfluidic devices are provided below together with explanations on their limitations. In a structure such as depicted in FIG. 1B (main channel with side connector and spotting target), the sample flowing (from left to right) enters only partially the side connector, leading to an air bubble entrapment, limited dissolution of dAbs and poor diffusion of dAbs from the side channel to main channel on the left side. Adding a plurality of side connectors (FIG. 1C) can accommodate more dAb solution but essentially the same problem as in FIG. 1B remains. In addition, here, the absence of direct convection of liquid through the areas containing the dAbs makes the diffusion of the dAbs variable because the diffusion of the dAbs is strongly dependent on the coordinates of the dAbs in the structures after they have been deposited and dried.

Therefore, the prior art structures of FIG. 1 have many drawbacks. Most importantly, one may realize that such structures do not allow for an easy and precise control of the dissolution profile of dAbs. There is accordingly a need for an improved microfluidic device.

BRIEF SUMMARY OF THE INVENTION

According to a first aspect, the present invention is embodied as a microfluidic device comprising: a flow inlet and a flow outlet; one or more bypass channels defining a first flow path toward the flow outlet; and an auxiliary channel defining a second flow path toward the flow outlet, comprising a reagent area adapted to receive a reagent, and joining at least one of the one or more bypass channels at a junction downstream from the reagent area with respect to the second flow path.

In other embodiments, the said device may comprise one or more of the following features:
  the microfluidic device is designed such that the auxiliary channel provides a smaller flow rate than a bypass channel at the junction;
  the microfluidic device is further designed to constrict a flow in the auxiliary channel, upstream from the reagent area;
  the auxiliary channel splits from at least one of the bypass channels at a split upstream from the reagent area and comprises a flow constriction area upstream from the reagent area and at the level of or downstream from the split;
  the one or more bypass channels, the auxiliary channel and the reagent area have a same depth;
  the width of each of the channels is on the order of 10 micrometers;
  The microfluidic device of any one of claims 1 to 5, wherein the width of each of the channels is between 10 and 100 micrometers;
  The microfluidic device of any one of claims 1 to 7, comprising several bypass channels, wherein:
    the auxiliary channel joins at least one of the bypass channels at a primary junction, the primary junction located downstream from the reagent area with respect to the second flow path; and
    the auxiliary channel joins at least one of the bypass channels at a secondary junction, the secondary junction located downstream from the primary junction, with respect to the second flow path;
  the auxiliary channel joins the bypass channels at respective secondary junctions, each of the secondary junctions located downstream from the primary junction, with respect to the second flow path;
  the primary and secondary junctions define a hierarchy of junctions;
  at least a subset of the bypass channels have similar transverse sections;

the auxiliary channel and at least a subset of the bypass channels have similar transverse sections; and
  the reagent area is inserted in the auxiliary channel, in line with a straight section of the auxiliary channel.

The invention is further embodied, in another aspect, as a method for operating a microfluidic device, comprising the steps of: providing the microfluidic device according to the invention; depositing a reagent in the reagent area of the microfluidic device, preferably by inkjet deposition; and letting a fluid flow from the flow inlet to the flow outlet, such as to carry the reagent downstream from the reagent area with respect to the second flow path.

This method preferably comprises a further step of monitoring a chemical reaction downstream from the junction, the chemical reaction occurring notably due to the carried reagent.

Devices and methods embodying the present invention will now be described, by way of non-limiting example, and in reference to the accompanying drawings.

For the sake of pedagogy and clarity, details or features represented in the appended drawings may deliberately be exaggerated, simplified, omitted or truncated, and are not necessarily to scale.

DETAILED DESCRIPTION OF THE INVENTION

As an introduction to the following description, it is first pointed at general aspects of the invention. The microfluidic device has a flow inlet and outlet, generally defining a flow direction. A bypass channel (or more) and an auxiliary channel are provided which respectively defines a first and a second flow path toward the same outlet. The auxiliary channel connects to a reagent area, i.e., designed to receive a reagent (e.g., chemical or biological, such as dAb). It further joins the bypass channel at the level of a junction downstream from the reagent area (with respect to the second flow path), e.g., like a T-junction. Such a solution provides a simple way of adapting the dissolution rate of the reagent.

For the sake of exemplification, embodiments of the present invention described below mostly refer to immunoassay devices. However, it shall be apparent to those skilled in the art that other microfluidic devices can be contemplated with similar features as described above.

Figure 2:
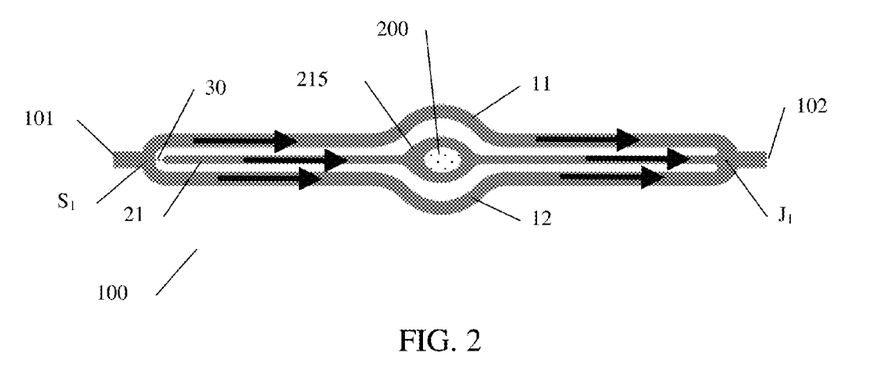
FIGS. 2-7 schematically illustrate channel structures of microfluidic devices according to various embodiments of the invention.
Figures 3A, 3B:
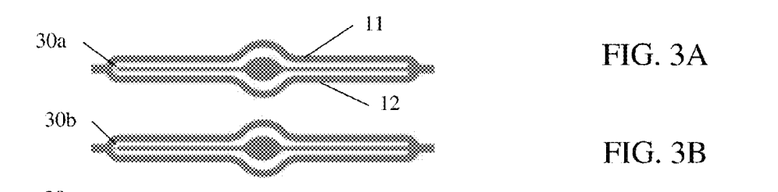
Figure 3C:
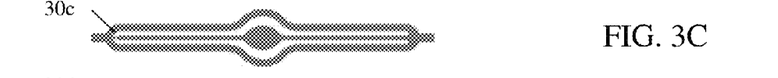
Figure 3D:
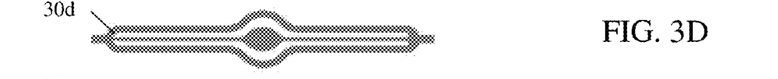
Figure 3E:
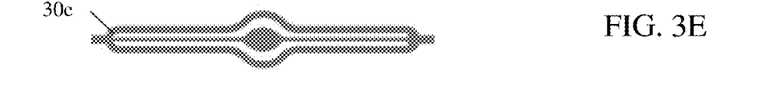

FIG. 2 schematically depicts a view of a device according to an embodiment. In reference to FIG. 2, the device 100 exhibits a channel structure with a flow inlet 101 and a flow outlet 102, bypass channels 11, 12 which define respective flow paths toward the outlet 102, as denoted by respective arrows. In fact, it follows from the general principle of the invention that only one bypass channel could be provided. This will be exemplified later.

The channel structure further exhibits an auxiliary channel 21, which defines another flow path toward the outlet. The latter can be referred to as the "second" flow path, as opposed to the "first" flow path defined by a bypass channel. The flow paths defined by all bypass channels can be regarded as one and a same, i.e., global flow path. As said, the auxiliary channel 21 is the channel that comprises the reagent area 215, which is itself designed to receive a reagent 200, e.g., dAbs. The reagent area can be designed similarly to that of FIG. 1.D.

Furthermore, as to be seen in FIG. 2, the auxiliary channel joins the bypass channels at the level of a junction $J_1$ located downstream from the reagent area (with respect to the second flow path).

Remarkably, having several types of channels, with the reagent (auxiliary) channel branching onto the bypass channel(s), provides a simple way of adapting the dissolution rate of the reagent. In other words, a larger volume of sample containing the reagent is effectively obtained after the junction, compared with methods such as discussed earlier. For example, the number of bypass channels might be adapted such as to obtain the desired dissolution rate, with transverse channel dimensions which possibly differ (like in FIG. 2), thereby allowing to further impact the dilution rate.

On the contrary, in variants, all channels may be provided with similar channel sections (including the auxiliary channel). In such a case, adding n bypass channels to one auxiliary channel amounts to multiply the volume of sample containing the reagent by n+1. Therefore, adding n bypass channels amounts to consider a flow rate divided by n+1 in each channel, implying smaller dissolution rates in fine.

The operation of the depicted device is quite simple. Reagent 200 is deposited in the area 215 of the microfluidic device, e.g., by inkjet deposition. Then, a fluid can be drawn from the inlet to the flow outlet, such as to carry the reagent downstream from the reagent area, as depicted by arrows. At the level of the junction $J_1$, the flows from the auxiliary and bypass channels merge, such that the effective dissolution rate measured downstream from the junction is decreased. A given chemical reaction can subsequently be monitored downstream from the junction, e.g., using suitable detection means (not shown).

In embodiments, the device is configured such that the auxiliary channel provides a smaller flow rate than the bypass fluid channel at the junction. This can for instance be achieved by increasing the number of bypass channels, as evoked earlier. Also, the device may be designed to constrict a flow in the auxiliary channel, e.g., upstream from the reagent area.

In practice, and as depicted in FIG. 2, one or more constriction areas 30 may be provided upstream from the reagent area 215. A constriction area may for instance simply be provided as a channel section smaller than other sections 11, 12, 21. Such an area 30 locally constricts the flow, which allows for tuning the desired dissolution rate.

Furthermore, in embodiments, the auxiliary channel typically splits from a bypass channels at the level of a split $S_1$, located upstream from the reagent area 215. In this regard, the flow constriction area 30 is conveniently located at the level of or downstream from the split $S_1$ (and upstream from the reagent area).

Providing constriction areas is however not mandatory. As said, the dissolution rate can be adapted by varying only the numbers or size of the bypass channels. In addition, in embodiments, the relative transverse dimensions of the bypass and auxiliary channels may differ, which also impacts the dissolution rate, without requiring any constriction area.

In other embodiments, one may not only provide constriction areas but, in addition, vary the relative transverse dimensions of the channels, as depicted in FIG. 2. The (relative) dimensions of the channels and/or the constriction areas can be tuned according to a trial and error method, and in accordance with the desired dissolution rates. Channels can for instance be obtained as open grooves engraved on a Silicon, PDMS or plastic surface, etc., following techniques known from microfluidics. When so doing, care should preferably be taken to keep a safe distance between the deposition zone 215 and the bypassing channels 11, 12. Examples are given below.

As further seen in FIG. 2, the reagent area is preferably in line with a straight section of the auxiliary channel (at variance with the solution of FIG. 1.B), such as to avoid a dead end channel linked to the deposition zone.

To summarize FIG. 2: the depicted design allows for easy spotting. In addition, even if an air bubble forms in one of the flow paths, this would not block the entire flow. The dissolution profile of reagent can be precisely set by varying the relative values of the flow resistances (denoted as $R_{11}$, $R_{12}$, and $R_{21}$) exhibited by the channels 11, 12, 21. Indeed, said resistances affect the flow rates of liquid in the different flow paths. The characteristic flow resistance of a structure can be defined as the ratio between the pressure applied to a liquid (assumed to be non-compressible) and the flow rate of the liquid in the structure. The flow resistance of a channel is primarily determined by its dimension and shape but other factors might also impact it. There is an analogy between flow resistances, flow rates and pressures and electrical circuits described using electrical resistances, current and electrical potentials: channels having equal shapes and lengths have equal flow resistances but they can be assembled in an architecture wherein they split, join, to form parallel and/or serial hydraulic circuits. Therefore, should identical channels be involved in a hydraulic circuit, it is possible to assemble them to affect the global flow resistance of the hydraulic circuit. For example, a central channel having a resistance $R_{21}$ will contribute less to the overall flow of liquid passing in a hydraulic circuit when it has parallel bypass channels having resistances $R_{11}/R_{12}$/etc. Increasing the number of bypass channels will increase sensitivity of a test by dissolving reagents in a larger volume fraction of sample, which will increase the time during which the sample and reagents will pass over receptors in the device. Conversely, decreasing $R_{21}$ with respect to $R_{11}/R_{12}/\ldots$ will favor the fast dissolution and exit of reagents in channel 21 toward receptors in the device within a small fraction volume of the sample. In this case, the time to result decreases (the signal can be read earlier). Finally, the design shown in FIG. 2 is a compact design, optimizing the useful surface where the channels are provided.

FIGS. 3A-E show examples of structures with various constrictions 30a-e to vary the dissolution profile of reagent. However, in general, a preferred geometry is a 10 micrometers wide constriction (the channels having a section wider than 10 micrometers in that case). For a given device, it is useful to calculate a characteristic dilution factor $\Theta$ as well as a dilution parameter $\sigma$, arbitrarily defined as follows:

$$\sigma = R_{reagent}/(R_{reagent}+R_{bypass}) = R_{reagent}/R_{total}$$

and $$\Theta = (1-\sigma)$$

The dilution factors $\Theta$ obtained typically vary from 0.04 (or 4%) to 0.85 (or 85%). A higher dilution factor corresponds to a higher dilution of the reagents, i.e. the reagents are present in a larger volume fraction of a sample.

Now, although such channel designs have generally been found satisfactory, constrictions might yet pose a challenge on the mass manufacture of chips (e.g., using plastic materials and mold injection/hot embossing).

Figure 4:
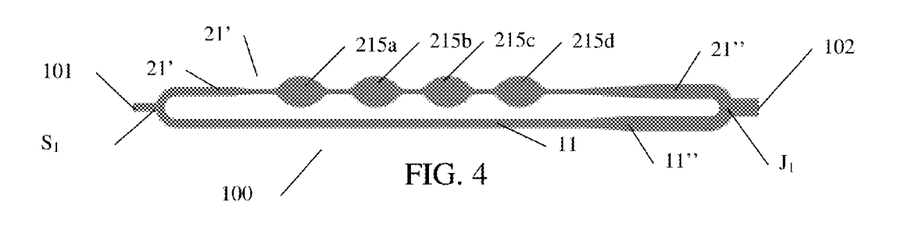

FIG. 4 relates to a particular embodiment with several deposition zones (reagent areas 215a-d) for accommodating larger amounts of reagent solution or several types of reagents. Only one bypass channel 11 is provided is that case. In addition, and at variance with FIG. 2 or 3, the channels may have non-constant sections 11", 21', 21", which also makes it possible to constrict a flow and/or adapt the effective dissolution rate. No constriction area is required in that case. Rather, slowly varying channel sections enable flow constriction.

FIGS. 5A-E pertain to other embodiments, where one or more bypassing channels are provided.

Figure 5A:
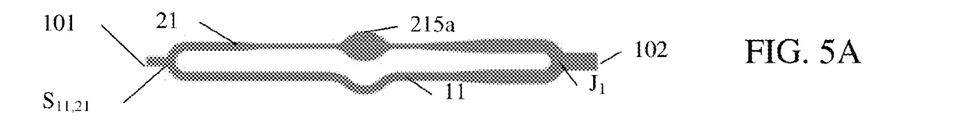

For example, in FIG. 5A, the channels 11, 21 have non-constant sections, just like in FIG. 4 In particular, the bypass channel section can be reduced on each side of the reagent area 215 such as to locally constrict the flow.

Figure 5B:
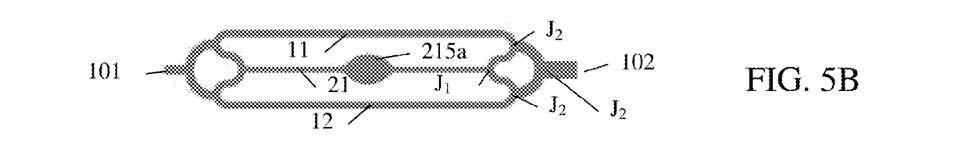
Figure 5C:
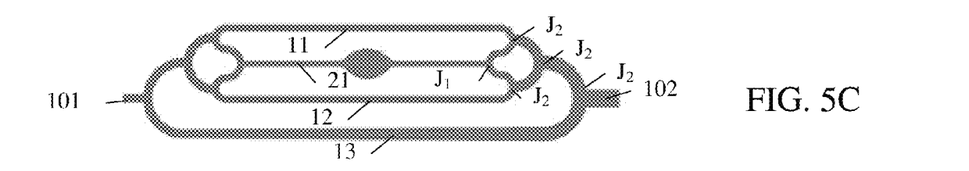
Figure 5D:
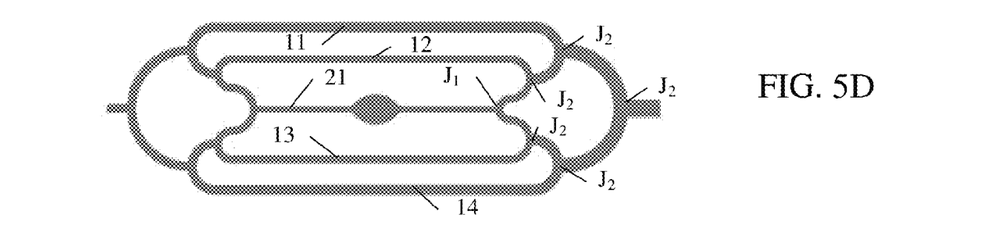

In FIGS. 5B and 5D, each channel has a constant section. The number of bypassing channels is increased compared to FIG. 5A.

Figure 5E:
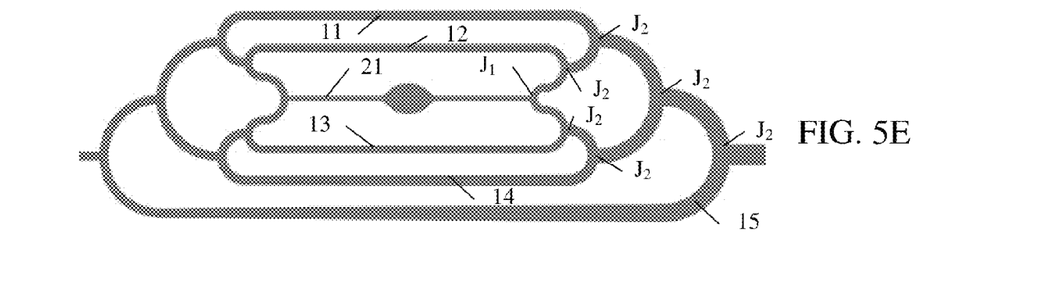

In FIG. 5C or 5E, the section of the lowest channel 13, 15 is not constant. Many other such variants can be contemplated. It remains that in each of the above cases, the auxiliary channel 21 joins at least one channel 11 amongst the bypass channels 11-15 at a junction $J_1$ downstream from the reagent area 215 (called primary junction) and upstream from a detection means (not shown), i.e., the latter downstream from the outlet 102. The channels further join at secondary junctions $J_2$ downstream from the primary junction.

As a note, one may question whether the auxiliary channel joins a bypass channel at the primary and/or at a secondary junction ($J_1$ or $J_2$). This however is a mere rhetorical question, and depends on the flow path considered. Considering a first flow path (defined by channel 11), one is tempted to conclude that channels 11 and 21 rejoin at $J_1$ rather than $J_2$. Considering the second flow path (defined by auxiliary channel 21), one would conclude the opposite. It remains that in all cases, the auxiliary channel joins at least one of the bypass channels at a junction downstream from the reagent area with respect to the second flow path. Furthermore, a secondary junction is located downstream from the primary junction, with respect to the second flow path (i.e., defined by the auxiliary channel).

In this regard, as represented in FIGS. 5B-E, the auxiliary channel 21 and the bypass channels 11, 12, . . . join at respective secondary junctions $J_2$. At each secondary junction, the reagent flow is further divided. The primary and secondary junctions further define an ordered hierarchy of junctions in that case. For symmetric bypass channels (FIGS. 5B and D), there are n+1 secondary junctions (n being the number of symmetric channels). Adding an outermost asymmetric channel results in an additional secondary junction, as in FIGS. 5C and E. Similarly, one may speak of a primary split (the closest to the auxiliary channel) vs. secondary splits (farther splits). With such designs, the diluted reagent flow (i.e., the second flow path) first divides at $J_1$, and then joins outermost bypass channels at $J_2$ junctions. Such designs makes it possible for easily predict dilution rates obtained in fine, without necessarily requiring flow constriction.

In some of the examples above, at least a subset of the bypass channels (if not all of them) have similar transverse sections (e.g., channels 11, 12 in FIGS. 5B and 5C), which makes the device easier to manufacture. In FIG. 5D, the outermost channels 11, 14 have similar dimensions. The same applies to the innermost bypass channels. In other cases, at least a subset of the bypass channels (and possibly the auxiliary channel) have similar transverse sections, like FIG. 5B, which is more suited for mass production. A distinct subset of bypass channels may have a different transverse section for fine-tuning the dissolution rate.

In the above cases, no small constriction needs to be fabricated (easier to manufacture). In addition, such designs lessen issues with clogging and particulates (if cells are in the sample, they will not be potentially broken by shear forces).

In addition, delay valves could be provided at all locations where air bubbles could form (e.g., at secondary junctions $J_2$, i.e., on the outlet side where liquid streams merge). In this respect, a valve preferably consists of two quarter-circle channels merging with an exit path having a width that is roughly double than that of the quarter-circle structures. Broadly, if a liquid comes from only one side in a single quarter-circle, it cannot proceed to the exit path but waits for liquid from the other quarter-circle. When liquids merge from both sides, filling proceeds toward the exit path. Such valves can further be added on top of each other.

Here, the volume (time) in which (during which) the reagent is dissolved is controlled by the contribution of each flow path to the stream of liquid leaving the overall deposition zone 215. The volumes and flow resistances of each of the paths do therefore matter.

The designs shown in FIG. 5 are scalable and transpose complex requirements into simple criteria (i.e., the contribution of the reagent flow path in channel 21 to the flow of liquid exiting the overall structures). Typically, the dilution factors obtained from the designs of FIG. 5 vary from 60% to 93%.

Figure 6:
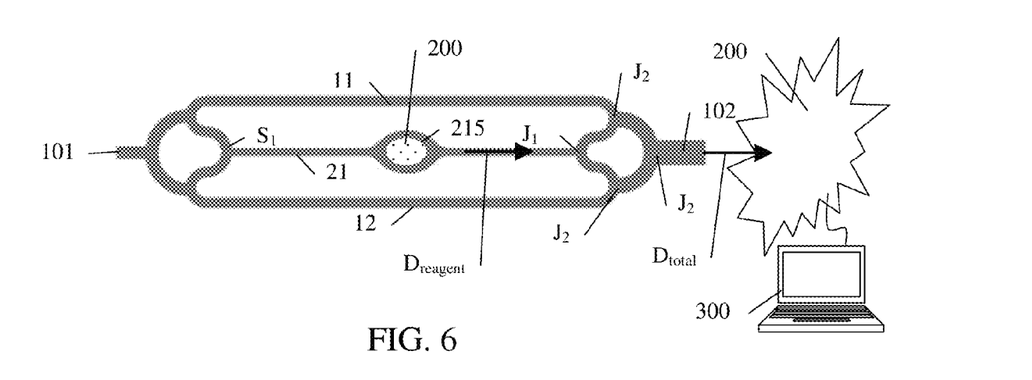

FIG. 6 relates to another embodiment, well suited for small/medium dilution factors, similar to that of FIG. 5B (i.e., two bypass channels 11, 12, one auxiliary channel 21 with in-line reagent area 215, and both primary $J_1$ and secondary junctions $J_2$). The arrows denotes reagent flow rate $D_{reagent}$ and total output flow rate $D_{total}$. In that case, all channels and the reagent area have a 60 micrometer depth. This can be achieved by engraving the channels and area at stake with a single depth on a chip. Having a single depth level ensures a simpler manufacture of the chip. The lateral dimensions of each of the channels are on the order of 10 micrometers ($\mu$m) in that case.

Such a design allows for a satisfactory filling with sample, as judged from tests performed using human serum. No bubble appeared to clog the exit path. In particular, spotting using inkjet 20 dAb solution drops of 180 picoliter (pL) each was easily achieved. A typical dilution factor obtained with such a design is $\Theta$=0.93 (or 93%), the dilution parameter $\sigma$=0.07, and the volume $V_{reagent}$ of the reagent area being about 4 nanoliter (nL). In that case, the reagent will be dissolved in at least 4/0.07=57 nL of sample.

In addition and as noted earlier, one may want to monitor 300 a chemical reaction 200 downstream from the junction, the reaction being triggered notably by the carried reagent. For example, the carried reagent can be a fluorescently-labeled dAb that binds specifically to an analyte present in the sample. The analyte-dAb pairs are captured by antibodies immobilized on the surface of channels downstream from the junction. Once captured, the analytes are detected by means of e.g., fluorescence because they are bound to a dAb. In this example, the chemical reaction 200 is a "sandwich" fluorescence surface immunoassay. Many other types of chemical or biochemical tests can be done as well. For example, DNA or RNA molecules, proteins, antigens, peptides, pathogens, pollutants, chemicals, toxins can be detected using reagents that are deposited in the deposition area 215 and dissolved using a chosen dilution parameter. Moreover, other types of signals than fluorescence can be used. For example, the reagent 200 can be fluorescently-labeled oligonucleotides, or a functionalized nanoparticles or colored latex particle. It can also be a dAb that is functionalized with an enzyme or gold nanoparticles, for example. More than one type of reagent 200 can be deposited alone or together with some salts, surfactants or chemicals in the deposition area 215. The role of the chemicals deposited can vary greatly as it can for example be a mixture of fluorescently-labeled dAbs with some enzymes for lysing pathogens, and chemicals such as sugars, which are used to improve the stability of dAb in the dry state in a manufactured device. A chemical can also be spotted over the spotted dAbs to further retard their dissolution and augment the dilution factor, if needed. Convenient detection means are therefore preferably involved (not shown), downstream from the outlet 102.

Figure 7:
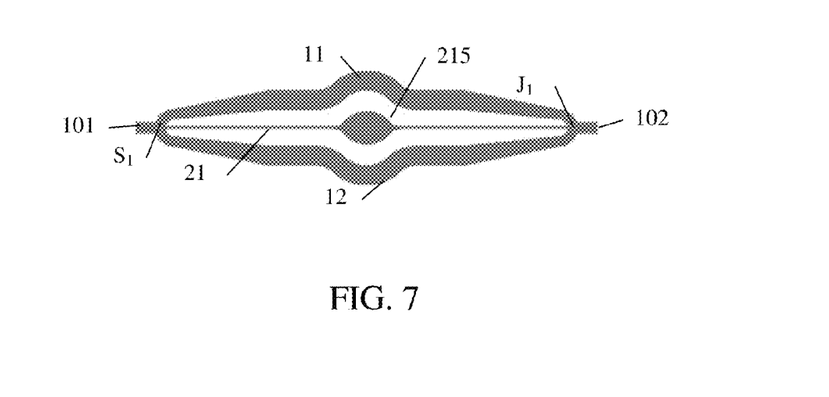

FIG. 7 relates to still another embodiment, this time most suited for high dilution. Here, the width of the channels varies between 10 and 100 micrometers. In particular, the section of the auxiliary channel 21 is roughly constant, about 10 micrometer wide, while the width of the bypass channels 11, 12 can reach 100 micrometers (their section is not constant, it passes from about 50 to 100 micrometers in that case). The reduction of the width of the channels 11 and 12 near $S_1$ and $J_1$ reduces the chances of having a liquid from stopping filling the device due to a sudden decrease of the capillary pressure (capillary pressure decreases when characteristics dimensions, e.g. the width of the channels here, increases). The dimensions of channels 11 and 12 near $J_1$ are, in addition, not reduced too much so as to keep a slight discontinuity in the filling behavior of the liquid. In order for the liquid to pass $J_1$, all liquid menisci from channels 21, 11 and 12 have to merge. This prevents the formation of an air bubble in the junctions. As evoked earlier, it was empirically found that when the width of a channel after a given junction is approximately twice as large as a channel before a junction, air bubbles do not form. Thus, a channel transverse section downstream from a junction may preferably be at least twice as large as the channel section upstream from that junction.

The channels are in this example further characterized by the following parameters. The flow resistances are:
For the bypass channel, $R_{11,12}=4\ 10^{17}\ m^{-3}$; and
For the auxiliary channel, $R_{21}=1.3\ 10^{15}\ m^{-3}$. Note that in an approximation using a circular pipe, one has $R=8L/(\pi r^4)$, where L is the length and r is the radius of the pipe, whence the units.

The dilution factor obtained is $\Theta=99.84\%$, for a reagent area volume $V_{reagent}$ of 3.2 nL. In that case, the reagent (e.g., dAb) will be dissolved in at least $3.2/0.0016=2\ \mu L$ of sample. While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims. For example, other materials than PDMS, silicon or plastic could be involved. Microfluidic devices such as described above may find numerous applications to immunoassays, DNA tests and tests that are based in general on the principal of ligand-receptor interactions wherein a ligand or a receptor is an analyte of interest. Many other variants can be contemplated. For instance, dissolution retarding species could be added in the reagent zone, in order to further tune the dissolution rates.

The invention claimed is:

1. A microfluidic device comprising:
a flow inlet and a flow outlet;
a bypass channel defining a first flow path away from the flow inlet and toward the flow outlet; and
an auxiliary channel defining a second flow path away from the flow inlet and toward the flow outlet,
wherein the auxiliary channel defines a reagent area adapted to receive a reagent,
wherein the auxiliary channel joins the bypass channel at a primary junction downstream from the reagent area and upstream from the flow outlet,
wherein a quarter-circle portion of the auxiliary channel joins a quarter-circle portion of the bypass channel at the primary junction to form a delay valve,
wherein the quarter-circle portion of the auxiliary channel and the quarter-circle portion of the bypass channel merge with an exit path having a greater width than a width of the quarter-circle portion of the auxiliary channel and a width of the quarter-circle portion of the bypass channel, and
wherein the auxiliary channel is adapted such that a flow rate of the auxiliary channel at the primary junction is smaller than a flow rate of the bypass channel at the primary junction.

2. The microfluidic device of claim 1,
wherein a portion of the auxiliary channel upstream from the reagent area defines a flow constriction area that constricts a flow of the second flow path relative to other areas in the portion of the auxiliary channel upstream from the reagent area.

3. The microfluidic device of claim 2,
wherein the auxiliary channel splits from the bypass channel at a split upstream from the reagent area, and
wherein the flow constriction area is arranged at or downstream from the split.

4. The microfluidic device of claim 1, wherein the bypass channel, the auxiliary channel and the reagent area have a same depth.

5. The microfluidic device of claim 1, wherein a width of each of the bypass channel and the auxiliary channel is between 10 and 100 micrometers.

6. The microfluidic device of claim 1,
further comprising a plurality of the bypass channel,
wherein the auxiliary channel joins at least one of the bypass channels at the primary junction, wherein the primary junction is located downstream from the reagent area, and
wherein the auxiliary channel joins at least one of the bypass channels at a secondary junction, wherein the secondary junction is located downstream from the primary junction.

7. The microfluidic device of claim 1,
further comprising a plurality of the bypass channel,
wherein at least a subset of the bypass channels have similar transverse sections.

8. The microfluidic device of claim 7,
wherein the auxiliary channel and the at least a subset of the bypass channels have similar transverse sections.

9. The microfluidic device of claim 1,
wherein the auxiliary channel is adapted to have a straight section, and
wherein the reagent area is defined in the straight section of the auxiliary channel.

10. A method comprising the steps of:
providing the microfluidic device according to claim 1;
depositing the reagent in the reagent area of the microfluidic device; and
letting a fluid flow from the flow inlet to the flow outlet to thereby carry the reagent downstream from the reagent area.

11. The method of claim 10,
further comprising a step of monitoring a chemical reaction downstream from the primary junction,
wherein the chemical reaction occurs due to the reagent carried by the fluid.

* * * * *